United States Patent [19]

De Maagd et al.

[11] Patent Number: 5,451,222
[45] Date of Patent: Sep. 19, 1995

[54] SMOKE EVACUATION SYSTEM

[75] Inventors: Donald R. De Maagd, deceased, late of Rockford, by Gloria A. Maagd legal representative; Jack A. Dekkinga, Jenison; Donald N. De Maagd, Grandville, all of Mich.

[73] Assignee: Desentech, Inc., Grand Rapids, Mich.

[21] Appl. No.: 213,568

[22] Filed: Mar. 16, 1994

[51] Int. Cl.⁶ ............................................. A61B 17/39
[52] U.S. Cl. .................................... 606/41; 604/22; 604/35; 606/45
[58] Field of Search ................ 606/37, 42, 45, 46; 604/22, 35

[56] References Cited

U.S. PATENT DOCUMENTS

| | | |
|---|---|---|
| 3,828,780 | 8/1974 | Morrison, Jr. . |
| 3,884,237 | 5/1975 | O'Malley et al. . |
| 3,902,494 | 9/1975 | Haberlen et al. . |
| 3,906,955 | 9/1975 | Roberts . |
| 3,974,833 | 8/1976 | Durden, III . |
| 4,307,720 | 12/1981 | Weber, Jr. . |
| 4,347,842 | 8/1982 | Beale . |
| 4,562,838 | 1/1986 | Walker . |
| 4,573,965 | 3/1986 | Russo ............................ 604/35 X |
| 4,683,884 | 8/1987 | Hatfield et al. . |
| 4,719,914 | 1/1988 | Johnson . |
| 4,846,790 | 7/1989 | Hornlein et al. ................. 604/22 |
| 4,850,352 | 7/1989 | Johnson . |
| 4,911,159 | 3/1990 | Johnson et al. . |
| 4,919,129 | 4/1990 | Weber, Jr. et al. . |
| 4,932,952 | 6/1990 | Wojciechowicz, Jr. . |
| 4,960,419 | 10/1990 | Rosenberg . |
| 5,035,695 | 7/1991 | Weber, Jr. et al. . |
| 5,055,100 | 10/1991 | Olsen . |
| 5,061,268 | 10/1991 | Fleenor . |
| 5,085,657 | 2/1992 | Ben-Simhon . |
| 5,088,657 | 2/1992 | Delahuerga et al. . |
| 5,098,430 | 3/1992 | Fleenor . |
| 5,122,153 | 6/1992 | Harrel .......................... 604/22 X |
| 5,133,714 | 7/1992 | Beane . |
| 5,154,709 | 11/1992 | Johnson . |
| 5,160,334 | 11/1992 | Billings et al. . |
| 5,181,916 | 1/1993 | Reynolds et al. . |
| 5,192,267 | 3/1993 | Shapira et al. . |
| 5,195,959 | 3/1993 | Smith . |
| 5,196,007 | 3/1993 | Ellman et al. ................... 606/45 X |
| 5,211,639 | 5/1993 | Wilk . |
| 5,215,522 | 6/1993 | Page et al. ...................... 604/35 X |
| 5,217,457 | 6/1993 | Delahuerga et al. . |
| 5,242,442 | 9/1993 | Hirschfeld ....................... 606/42 |
| 5,224,944 | 7/1993 | Elliott ............................ 604/35 X |
| 5,234,428 | 8/1993 | Kaufman . |
| 5,244,462 | 9/1993 | Delahuerga et al. . |
| 5,256,138 | 10/1993 | Burek et al. . |
| 5,269,781 | 12/1993 | Hewell, III . |
| 5,279,599 | 1/1994 | Wilk . |
| 5,300,069 | 4/1994 | Hunsberger et al. . |
| 5,310,406 | 5/1994 | Sharpe et al. ................... 604/35 |

*Primary Examiner*—Peter A. Aschenbrenner
*Attorney, Agent, or Firm*—Price, Heneveld, Cooper, DeWitt & Litton

[57] ABSTRACT

A smoke evacuation system is provided for attachment to a surgical desiccator, the surgical desiccator including a desiccator body forming a handle and a cauterizing tip for searing tissue to reduce bleeding. The smoke evacuation system includes a section of tube connected to a suction unit, a front retainer and a rear retainer for holding the tube to the body in a position such that the tube and the desiccator body can be cradled in a surgeon's hand, and a suction tip attachable to the front retainer in a non-interfering position proximate the cauterizing tip. The front retainer defines a passageway connecting the suction tip to the section of tube such that smoke, odors and biological contaminants generated by the cauterizing tip can be efficiently suctioned away through the suction tip, the retainer and the tube by the suction unit. The front retainer releasably engages suction tips for easy replacement of the suction tips for sterility and so that a particular suction tip can be selected to correspond to a particular cauterizing tip. The front retainer comprises two halves which define a first recess therebetween for supporting a nipple to engage the section of tube, a second recess therebetween for supporting an insert to engage the desiccator, and a third recess therebetween defining a passageway between the suction tip and the section of tube for placing the suction tip and the section of tube in gaseous communication. A desiccator incorporating the section of tube and utilizing the suction tips is also disclosed.

20 Claims, 3 Drawing Sheets

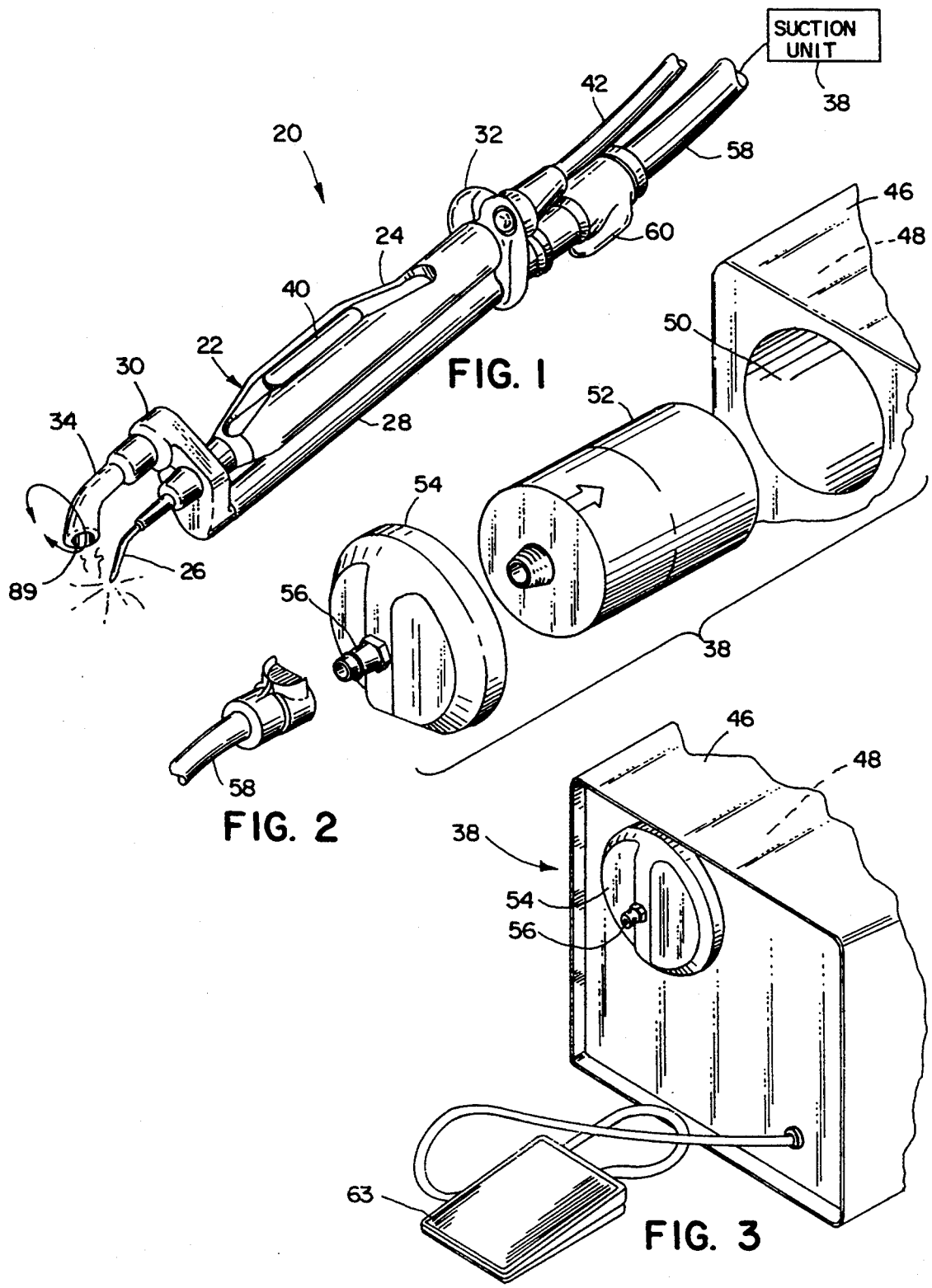

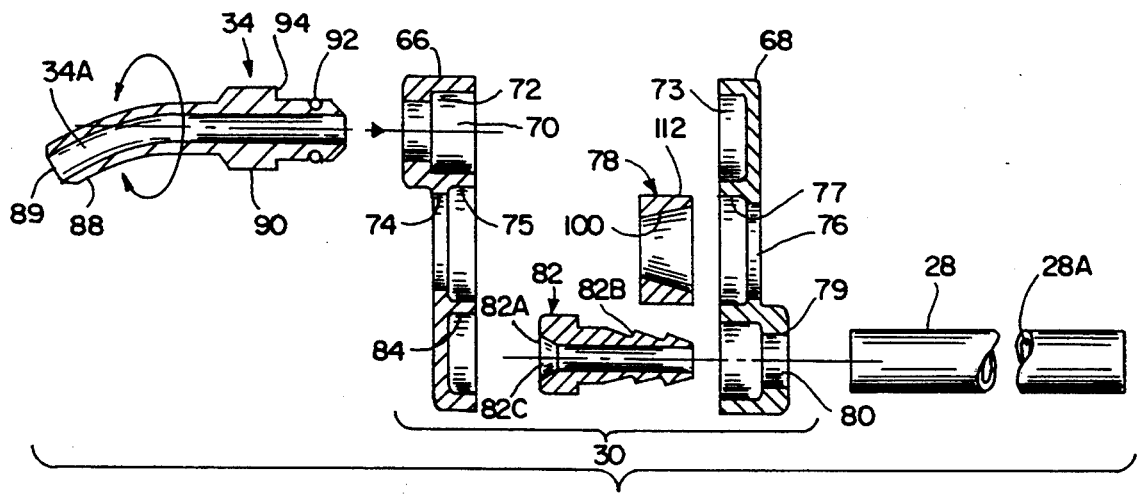
FIG. 4
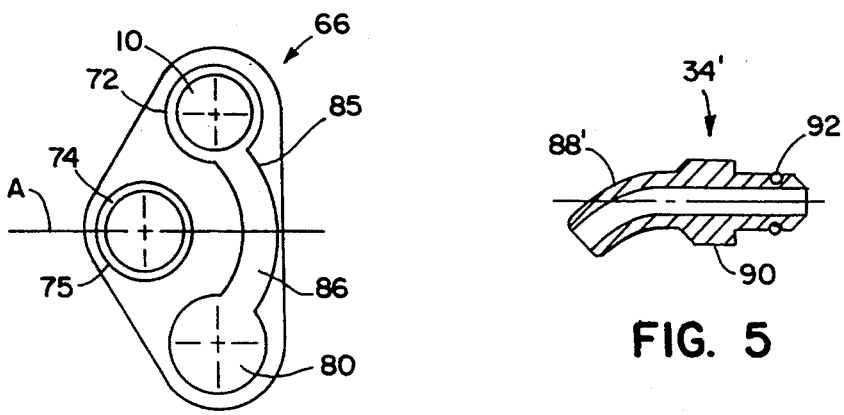
FIG. 4A
FIG. 5
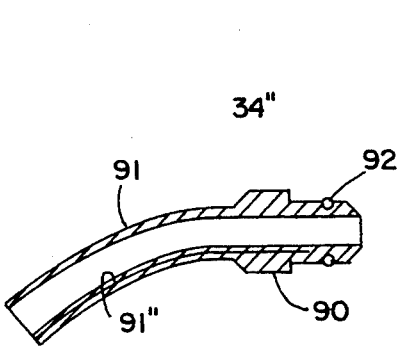
FIG. 5A
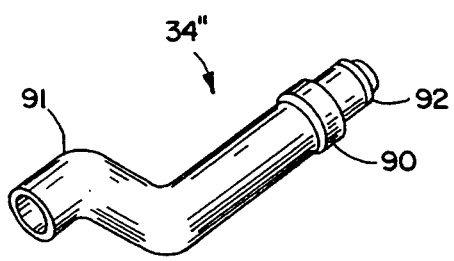
FIG. 5B

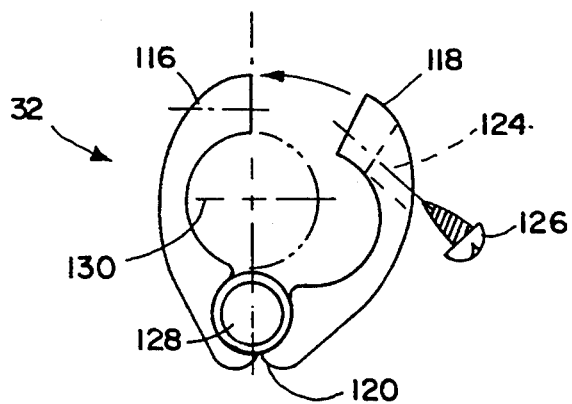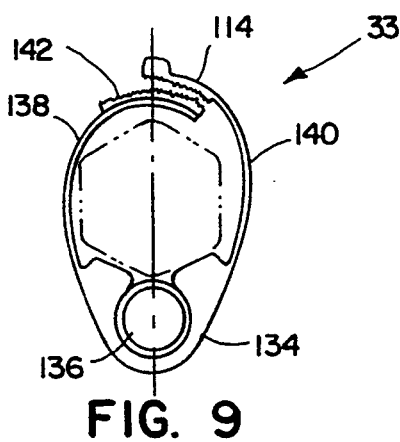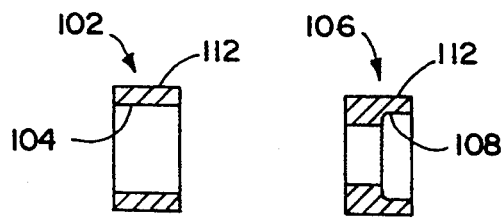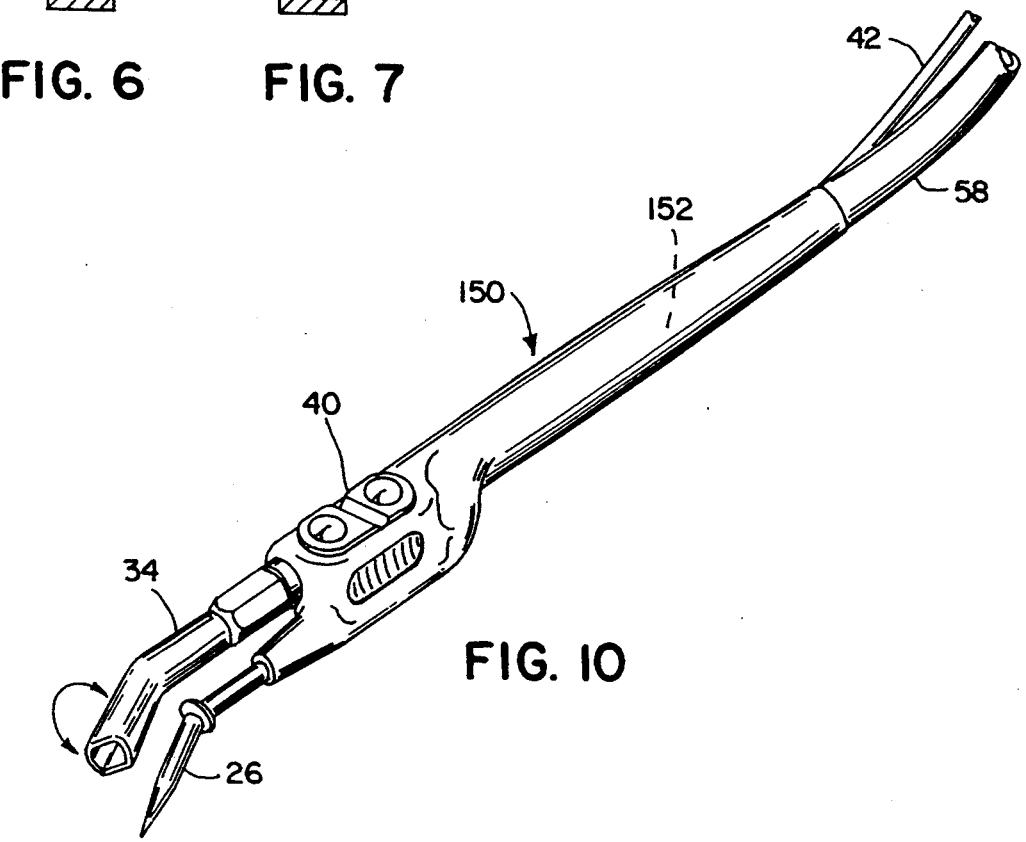

5,451,222

SMOKE EVACUATION SYSTEM

BACKGROUND OF THE INVENTION

The present invention relates to medical devices, and in particular to a smoke evacuation system attachable to a medical device.

Several different smoke evacuation systems are known for removing smoke generated by a cauterizing tip of a desiccator. However, many smoke evacuation systems are undesirably bulky and/or difficult to handle with the precision and dexterity needed when operating a medical device such as a desiccator. Further, most smoke evacuation systems are not adapted for attachment to various desiccator sizes and styles, nor adapted to be adjustable so as to efficiently gather smoke when used with various cauterizing tip configurations. Concurrently, it is also important that the system be inexpensive to manufacture, easy to assemble and adjust, and also easy to clean and/or replace parts so that it will be kept clean to maintain a sterile environment around the desiccator. Thus, a smoke evacuation system solving these problems is desired.

SUMMARY OF THE INVENTION

In one aspect, the present invention includes smoke evacuation system for attachment to a surgical desiccator. The smoke evacuation system includes an elongated member defining a first passageway including an outlet configured for attachment to a suction unit, and a suction tip defining a second passageway including an inlet. A retainer is provided for securing the elongated member and the suction tip to the desiccator with said elongated member being positioned generally adjacent the body of the desiccator and the suction tip inlet being positioned proximate a cauterizing tip of the desiccator. The retainer places the first and second passageways in communication so that, by suctioning air from the elongated member outlet, air is drawn into the suction tip inlet along with smoke, odors and biological contaminants generated by the cauterizing tip. In a preferred form, the retainer includes an insert for mateably engaging a front of the desiccator, the insert being selected from a plurality of inserts configured to engage different desiccator shapes.

These and other features, advantages and objects of the present invention will be further understood and appreciated by those skilled in the art by reference to the following specification, claims and appended drawings.

BRIEF DESCRIPTION OF THE DRAWINGS

FIG. 1 is a perspective view of a smoke evacuation system and desiccator embodying the present invention;

FIG. 2 is an exploded view of a suction unit for use with the smoke evacuation system shown in FIG. 1;

FIG. 3 is a perspective view of the suction unit shown in FIG. 2;

FIG. 4 is an exploded cross-sectional side view of the front retainer shown in FIG. 1;

FIG. 4A is an inside end view of the front half of the front retainer shown in FIG. 4;

FIG. 5 is a side cross-sectional view of an alternative suction tip that can be releasably engaged with the front retainer shown in FIG. 4;

FIG. 5A is a side cross-sectional view of another alternative suction tip which is deformable and which is configured for use with the front retainer shown in FIG. 4;

FIG. 5B is a perspective view of the suction tip shown in FIG. 5A, the suction tip being shown as deformed into an S-shaped configuration;

FIGS. 6–7 are side cross-sectional view of alternative inserts that can be removably retained in the front retainer shown in FIG. 4;

FIG. 8 is an end view of the rear retainer shown in FIG. 1, the rear retainer including a living hinge;

FIG. 9 is an end view of a modified rear retainer, the retainer including straps having hook-and-loop material thereon for securing the rear retainer to a desiccator; and FIG. 10 is a perspective view of a desiccator embodying the present invention in which a smoke evacuation passageway has been incorporated integrally into the desiccator, the desiccator including a front section configured to releasably receive a suction tip identical to the suction tips disclosed above.

DETAILED DESCRIPTION OF PREFERRED EMBODIMENTS

A smoke evacuation system 20 (FIGS. 1–3) embodying the present invention is configured for retrofit attachment to a surgical desiccator 22. Desiccator 22 includes a body 24 defining a handle and a cauterizing tip 26 for use during a surgical operation. Smoke evacuation system 20 includes a section of tube 28, a pair of retainers 30 and 32 for retaining the tube 28 to desiccator body 24. A suction tip 34 is supported by front retainer 30 so that, when system 20 is attached to desiccator 22, suction tip 34 is optionally positioned relative to cauterizing tip 26. Front retainer 30 defines a passageway 36 operably connecting suction tip 34 to tube 28, and tube 28 is connected to a suction unit 38 so that smoke, odors and biological contaminants generated by a cauterizing tip 26 can be drawn into suction tip 34 and through components 30 and 28 to suction unit 38.

Desiccator body 24 (FIG. 1) is generally elongated and shaped so that it can be conveniently cradled in a medical worker's hand. Cauterizing tip 26 extends forwardly of desiccator body 24 so that, with the desiccator in the medical worker's hand, cauterizing tip 26 can be accurately manipulated to perform a medical operation. An electrical switch 40 and power cord 42 are connected to cauterizing tip 26 in a position such that electrical switch 40 can be conveniently actuated by the worker to energize and heat cauterizing tip 26 for use. The comfort and shape of desiccator 22 and in particular the convenience and ease of use are particularly important to medical workers using desiccator 22. Also, the location and style of cauterizing tip 26 is important to many medical professionals, and it is important that these features not be interfered with visually or physically.

Suction unit 38 (FIGS. 2–3) includes a housing 46 and a suctioning pump 48 located within housing 46. Housing 46 includes a recess 50, and a filter cartridge 52 for removing airborne particles and also odors is located in recess 50. An adapter cover 54 covers recess 50, cover 54 including a connector 56 for connecting to a flexible hose 58. Flexible hose 58 includes a releasable connector 60 configured to engage a mating connector 62 on the rear end of tube section 28. A 7foot pedal switch 63 is operably connected to suction unit 38 for selectively operating suction unit 38.

Front retainer 30 (FIG. 4) includes a front and a rear shell member or half 66 and 68, respectively. Front half 66 includes material defining a hole 70 for releasably receiving suction tip 34, and further includes a suction tip engaging supporting surface 72 for supporting suction tip 34 in the retained position. Rear half 68 includes a corresponding recess 73. Front and rear halves 66 and 68 further include aperture forming surfaces 74 and 76, respectively including insert support surfaces 75 and 77, respectively, that are configured to receive and stably support an insert 78. Insert 78 is ring-shaped and is configured to engage and support a front tapered end on desiccator body 24. Rear half 68 includes a first nipple engaging support 79 defining an aperture 80 for receiving a robe engaging nipple 82, and front half 66 includes a corresponding second nipple engaging support 84. Nipple 82 includes an enlarged end 82A that is supported between supports 79 and 84. Nipple 82 further includes a projecting end 82B including angled barb-like surfaces for securely engaging tube 28. A passageway 82C extends through nipple 82. Walls 85 (FIG. 4A) on front half 66 and rear half 68 define a passageway 86 which extends between holes 70 and aperture 80. Passageway 86 places the passageway 34A in suction tip 34 (FIG. 4) in gaseous communication with the passageway 82C in nipple 82. Thus, smoke can be drawn through suction tip 34, retainer 30 and tubes 28 and 58 to suction unit 38 (FIG. 1). It is noted that the illustrated front and rear halves 66 and 68 are identical in shape. This becomes apparent if, for example, front retainer 66 is pivoted 180° about axis A. (See FIGS. 4 and 4A.)

Suction tip 34 (FIG. 4) includes a protruding end 88 including an inlet 89 to passageway 34A and a retainer engaging end 90. Retainer engaging end 90 includes a resilient "O"-ring seal 92 configured to frictionally and sealingly engage hole 70 in front retainer 30. A lip 94 on end 90 prevents over-insertion of suction tip 34 into retainer 30. Suction tip 34 can be rotated in retainer 30 so that the inlet 89 on protruding end 88 can be positioned for optimal suctioning and removal of smoke from cauterizing tip 26. Suction tip passageway 34A extends continuously from inlet 89 through protruding end 88 and retaining end 90.

It is contemplated that a variety of different suction tips 34 can be provided so that a particular suction tip 34 can be selected to position the inlet 96 of suction tip 34 optimally proximate cauterizing tip 26 of desiccator 22. For example, FIG. 5 shows a modified suction tip 35 which includes a retaining end 90 identical to suction tip 34, and further includes a protruding end 88' having a shorter dimension than protruding end 88 of suction tip 34. A second style suction tip 34" is shown in FIGS. 5A and 5B. Suction tip 34" includes a retaining end 90 identical to suction tip 34, and further includes a protruding end 88" having a deformable tube 91 and a wire 91" to hold the desired shape once tube 91 is deformed. For example, in FIG. 5B the deformable tube 91 has been deformed to an S shape configuration.

It is also contemplated that various inserts can be positioned within front retainer 30 to engage different shapes and styles of desiccator bodies 24. Insert 78 (FIG. 4) includes a frusto-conically-shaped inner surface 100 for engaging a similarly shaped front nose on body 24 of desiccator 22. Alternative modified insert 102 (FIG. 6) includes a cylindrically-shaped inner surface 104, and a second modified insert 106 (FIG. 7) includes a stepped inner surface 108. Each inserts 78, 102 and 106 include a ring-shaped outer wall having a cylindrically-shaped outer surface 112 for mateably securely engaging the insert supports 75 and 77 on front and rear halves 66 and 68.

Rear retainer (FIG. 8) includes a right hand link 116 and a left hand link 118 interconnected by a living hinge 120, Link 116 includes a hole 122 at an end opposite living hinge 120, and link 118 includes a corresponding hole 124 that aligns with hole 122. A screw 126 can be extended through hole 124 threadably into hole 122 to secure links 116 and 118 together. When secured together, the inner surfaces of links 116 and 118 define a first aperture 128 for securely retaining tube 28, and a second aperture 130 for securely engaging desiccator body 24 to retain tube 28 to body 24.

A modified rear retainer 33 is shown in FIG. 9. Modified rear retainer 33 includes a lower section 134 defining an aperture 136 for securely engaging and holding tube 28. A pair of straps 138 and 140 extend upwardly from the sides of section 134. Straps 138 and 140 include hook-and-loop material 142 and 144 that can be engaged as straps 138 and 140 are wrapped around desiccator body 24.

As can be seen, front and rear retainers 30 and 32 are adaptable to fit different shapes and styles of desiccator bodies 24, such that smoke evacuation system 20 can be retrofittably attached to a variety of different desiccators 22. Further, a particular suction tip can be selected from a plurality of different suction tips (such as tips 34 and 35) so that the position of the inlet 89 to suction tip 34 optionally proximate cauterizing tip 26 of desiccator 22 regardless of the shape of cauterizing tip 26. Notably, smoke evacuation system. 20 attaches to a desiccator 22 in a manner that facilitates cradling the desiccator 22 in a medical worker's band even with the smoke evacuation system 20 attached thereto. Further, suction tip 34 is located in a position where it will not interfere with the body tissue being operated on, and further in a position where it will not interfere with the vision of the medical worker utilizing desiccator 22. Notably, by actuation of foot pedal switch 63, suction unit 38 is operated to draw in smoke odors and biological contaminants generated by cauterizing tip 26 such that the medical worker is not exposed to these substances. Further, the smoke, odor and biological contaminants drawn into smoke evacuation system 20 are drawn through a filter 52 where they are treated or collected as desired. Still further, suction tips 34 (and also system components 28, 30 and 32) can be made disposable or autoclavable for maintaining a sterile environment.

A modified desiccator 150 (FIG. 10) incorporates a passageway 152 into the desiccator body 24. The front of desiccator 150 is configured to operably connect to and support cauterizing tip 26 and also suction tips 34 (and 34' and 34"). Smoke evacuation tube 58 and an electrical cord 42 extend from the rear end of desiccator 150.

In the foregoing description, it will be readily appreciated by those skilled in the art that modifications may be made to the invention without departing from the concepts disclosed herein. Such modifications are to be considered as included in the following claims, unless these claims by their language expressly state otherwise.

The embodiments of the invention in which an exclusive property or privilege is claimed are defined as follows:

1. A smoke evacuation system for attachment to a surgical desiccator, comprising:

an elongated member defining a first passageway including an outlet configured for attachment to a suction unit;

a suction tip defining a second passageway including an inlet; and a retainer configured to secure said elongated member and said suction tip to a desiccator with said elongated member being positioned generally adjacent a body of the desiccator and said suction tip inlet being positioned proximate a cauterizing tip of the desiccator, said retainer placing said first and second passageways in communication so that, by suctioning air from said elongated member outlet, air is drawn into said suction tip inlet along with smoke, odors and biological contaminants generated by the cauterizing tip, said retainer including insert retaining surfaces; and an insert shaped to mateably engage a from end of the desiccator body and to be securely supported by said insert engaging surfaces.

2. A smoke evacuation system as defined in claim 1 wherein said retainer defines a third passageway operably connecting said first and second passageways.

3. A smoke evacuation system as defined in claim 2 wherein said retainer includes first and second supports located generally on opposite sides of the desiccator body for securely retaining said suction tip and said elongated member, respectively, said third passageway extending between said first and second supports for operably connecting said first and second passageways.

4. A smoke evacuation system a defined in claim 1 wherein said retainer includes insert retaining surfaces, and including an insert shaped to mateably engage a front end of the desiccator body and to be securely supported by said insert engaging surfaces.

5. A smoke evacuation system as defined in claim 1 including a plurality of said suction tips, said suction tips each being configured to releasably engage said retainer.

6. A smoke evacuation system as defined in claim 1 including a second retainer spaced frown said first retainer, said second retainer being configured to engage the desiccator body and to hold said elongated member adjacent the desiccator body.

7. A smoke evacuation system as defined in claim 1 wherein said retainer includes nipple supporting surfaces, and including a nipple positioned and secured to said retainer by said nipple engaging surfaces, said nipple being configured to engage said elongated member.

8. A smoke evacuation system for attachment to a surgical desiccator, comprising:

an elongated member defining a first passageway including an outlet configured for attachment to a suction unit;

a suction tip defining a second passageway including an inlet;

a first retainer configured to secure said elongated member and said suction tip to a desiccator with said elongated member being positioned generally adjacent a body of the desiccator and said suction tip inlet being positioned proximate a cauterizing tip of the desiccator, said retainer defining an airtight intermediate passageway placing said first and second passageways in communication so that, by suctioning air from said elongated member outlet, air is drawn into said suction tip inlet along with smoke, odors and biological contaminants generated by the cauterizing tip, said first retainer defining a hole configured to mateably engage a front nose of the desiccator body along a longitudinal direction defined by the hole;

said intermediate passageway extending generally transversely to said longitudinal direction and extending circumferentially, partially around the hole; and a second retainer spaced from said first retainer configured to engage and hold said elongated member adjacent the body of the desiccator, said second retainer including a pair of opposing half sections and a hinge connecting said opposing half sections.

9. A smoke evacuation system for attachment to a surgical desiccator, comprising:

an elongated member defining a first passageway including an outlet configured for attachment to a suction unit;

a suction tip defining a second passageway including an inlet; and a retainer configured to secure said elongated member and said suction tip to a desiccator with said elongated member being positioned generally adjacent a body of the desiccator and said suction tip inlet being positioned proximate a cauterizing tip of the desiccator, said retainer defining an airtight intermediate passageway placing said first and second passageways in communication so that, by suctioning air from said elongated member outlet, air is drawn into said suction tip inlet along with smoke, odors and biological contaminants generated by the cauterizing tip, said retainer including an aperture configured to mateably engage a front nose of the desiccator along a longitudinal direction defined by the aperture, said retainer including mating half sections that can be secured together along said longitudinal direction to define said intermediate passageway.

10. A smoke evacuation system as defined in claim 1 wherein said retainer includes material defining a first aperture for releasably receiving and holding said suction tip, material defining a second aperture for receiving a nipple to engage said elongated member, material defining a passageway placing said first and second passageways in communication, and material defining a third aperture for receiving an insert to securely engage a front end of the desiccator body.

11. A smoke evacuation system for attachment to a surgical desiccator, comprising:

an elongated member defining a first passageway including an outlet configured for attachment to a suction unit;

a suction tip defining a second passageway including an inlet; and a retainer configured to secure said elongated member and said suction tip to a desiccator with said elongated member being positioned generally adjacent a body of the desiccator and said suction tip inlet being positioned proximate a cauterizing tip of the desiccator, said retainer placing said first and second passageways in communication so that, by suctioning air from said elongated member outlet, air is drawn into said suction tip inlet along with smoke, odors and biological contaminants generated by the cauterizing tip, said retainer defines a first aperture for releasably receiving and holding said suction tip, defines a second aperture for receiving a nipple to engage said elongated member, defines a passageway placing said first and second passageways in communication, and defines a third aperture for receiving an insert to securely engage a front end of the desiccator body; and a plurality of inserts positionable in said third aperture, the plurality of inserts being configured to engage different desiccator body shapes.

12. A smoke evacuation system for a desiccator, comprising:

a tube defining a first passageway;

a front retainer and a rear retainer for securing said tube to a desiccator; and a suction tip releasably engaged with said front retainer, said suction tube defining a second passageway which is placed in communication with said first passageway by said front retainer so that smoke generated at a tip of the desiccator can be drawn into said second passageway and through said first passageway to a suction unit attached to said tube, said front retainer including an insert shaped to releasably engage a front end of the desiccator.

13. A smoke evacuation system as defined in claim 12 wherein said front retainer defines a third passageway operably connecting said first and second passageways.

14. A smoke evacuation system as defined in claim 14 wherein said front retainer includes first and second supports for said suction tip and said tube located generally on opposite sides of the desiccator for retaining said tube and said suction tip, respectively, said first and second supports positioning said suction tip and said tube in locations chosen to provide comfort and maximum unobstructed vision to a medical worker using the desiccator.

15. A smoke evacuation system as defined in claim 14 including a plurality of said suction tips configured to match a corresponding cauterizing tip, said suction tips each including an inlet and being configured to position said inlet proximate the corresponding cauterizing tip when a selected one of said suction tip is engaged with said front retainer and the corresponding cauterizing tip is engaged with the desiccator.

16. A retainer for a smoke evacuation system, comprising:

a tube engaging nipple;

an insert configured to securely engage a medical device; and a retainer body defining a first aperture for releasably engaging a suction tip, defining a second aperture for supporting said tube engaging nipple, and defining a third aperture for supporting said insert, said retainer body defining a passageway that extends between said first aperture and said second aperture for placing a suction tip in gaseous communication with said tube engaging nipple.

17. A retainer as defined in claim 16 wherein said retainer body includes opposing halves that matingly engage.

18. A retainer as defined in claim 17 wherein said insert is ring-shaped, and is secured between said opposing halves.

19. A retainer as defined in claim 16 including a suction tip configured to releasably engage said material defining said first aperture.

20. A retainer as defined in claim 19 wherein said materials defining said first aperture and said second aperture are positioned on generally opposite sides of said third aperture.

* * * * *

UNITED STATES PATENT AND TRADEMARK OFFICE
CERTIFICATE OF CORRECTION

PATENT NO. : 5,451,222
DATED : September 19, 1995
INVENTOR(S) : Donald R. De Maagd (deceased); Jack A. Dekkinga It is certified that error appears in the above-indentified patent and that said Letters Patent is hereby corrected as shown below:

Column 2, line 34;
   "optionally" should be --optimally--.

Column 2, line 66;
   After "A" delete "7".

Column 3, line 15;
   "robe" should be --tube--.

Column 4, line 31;
   "optionally" should be --optimally--.

Column 4, line 35;
   "band" should be --hand--.

Column 5, claim 1, line 18;
   "from" should be --front--.

Column 5, claim 4, line 31;
   "a" should be --as--.

UNITED STATES PATENT AND TRADEMARK OFFICE
CERTIFICATE OF CORRECTION

PATENT NO. : 5,451,222
DATED : September 19, 1995
INVENTOR(S) : Ronald R. De Maagd (deceased); Jack A. Dekkinga It is certified that error appears in the above-indentified patent and that said Letters Patent is hereby corrected as shown below:

Column 5, claim 4, lines 32-35;
 delete "wherein said retainer includes insert retaining surfaces, and including an insert shaped to mateably engage a front end of the desiccator body and to be securely supported by said insert engaging surfaces." and insert --including a plurality of said inserts, each being configured to engage different desiccator body shapes.--.

Column 5, claim 6, line 41;
 "frown" should be --from--.

Column 7, claim 14, line 26;
 "claim 14" should be --claim 12--.

Column 8, claim 15, line 1;
 "claim 14" should be --claim 12--.

Signed and Sealed this

Seventh Day of May, 1996

Attest:

BRUCE LEHMAN

*Attesting Officer*    Commissioner of Patents and Trademarks